United States Patent
DiFoggio

(10) Patent No.: US 9,952,350 B1
(45) Date of Patent: Apr. 24, 2018

(54) OSCILLATING PATH LENGTH SPECTROMETER

(71) Applicant: BAKER HUGHES INCORPORATED, Houston, TX (US)

(72) Inventor: Rocco DiFoggio, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days.

(21) Appl. No.: 15/495,512

(22) Filed: Apr. 24, 2017

(51) Int. Cl.
| | |
|---|---|
| *G01N 21/00* | (2006.01) |
| *G01V 8/16* | (2006.01) |
| *G01J 3/457* | (2006.01) |
| *G01J 3/02* | (2006.01) |
| *E21B 49/08* | (2006.01) |

(52) U.S. Cl.
CPC .............. *G01V 8/16* (2013.01); *E21B 49/087* (2013.01); *G01J 3/0218* (2013.01); *G01J 3/457* (2013.01); *E21B 2049/085* (2013.01)

(58) Field of Classification Search
CPC . G01N 2035/00237; G01N 2035/1037; G01N 2035/1069; G01N 35/1067; G01N 35/1074; G01N 27/622; G01N 15/0826; G01N 2015/086; G01N 2021/317; G01N 21/0303; G01N 21/255; G01N 21/31; G01N 21/6486
See application file for complete search history.

(56) References Cited

U.S. PATENT DOCUMENTS

| | | |
|---|---|---|
| 4,664,522 A | 5/1987 | LeFebre |
| 4,786,171 A | 11/1988 | LeFebre et al. |
| 7,826,050 B2 | 11/2010 | DiFoggio et al. |
| 8,145,064 B2 | 3/2012 | Majewski et al. |
| 2005/0099618 A1* | 5/2005 | DiFoggio ................ E21B 47/06 356/70 |
| 2007/0013911 A1* | 1/2007 | DiFoggio ................ E21B 49/10 356/436 |

(Continued)

OTHER PUBLICATIONS

Cheng, J., et al., "A Digital Lock-in Amplifier for Use at Temperatures".

(Continued)

*Primary Examiner* — Michael P Stafira
(74) *Attorney, Agent, or Firm* — Mossman, Kumar & Tyler, PC

(57) ABSTRACT

Evaluating a fluid, including transmitting a light beam through the fluid to a detector while oscillating a path length traveled through the fluid by the light beam at a first frequency of oscillation; measuring a time-dependent intensity of incident light at the detector responsive to an interaction of the light beam with the fluid to produce a time-dependent intensity signal; filtering the time-dependent intensity signal to recover a path-dependent signal oscillating at the first frequency and indicative of an absorbance property of the fluid; and estimating a parameter of interest of the fluid using the path-dependent signal. The time-dependent intensity may be indicative of the true absorbance at multiple wavelengths of the fluid or fluids over the maximum path length difference so as to permit quantification of the percentages of each of these fluids. Filtering may include frequency filtering alone or using a phase-sensitive lock-in amplifier.

15 Claims, 7 Drawing Sheets

(56) References Cited

U.S. PATENT DOCUMENTS

2008/0154128 A1* 6/2008 Milner ................. A61B 5/0066
600/427
2016/0324403 A1* 11/2016 Yeoh, IV ........... A61B 1/00165

OTHER PUBLICATIONS

Stanford Research Systems, Inc.—Chapter 18—Signal Detection and Analysis.
www.thinkSRS.com—About Lock-in Amplifiers.
PHYS 331 Junior Physics Laboratory—Notes on Noise Reduction.
Analog Devices MT-086 Tutorial.
Lock in Amplifiers.

* cited by examiner

OSCILLATING PATH LENGTH SPECTROMETER

FIELD OF THE DISCLOSURE

This disclosure generally relates to compositional analysis of a fluid, especially a flowing fluid with time-varying composition, via spectroscopic analysis. More particularly, aspects of the disclosure relate to instances where the fluid is non-uniformly separated.

BACKGROUND OF THE DISCLOSURE

Procedures using what is commonly known as the "Beer-Lambert Law," (often just called "Beer's Law") are well known, which law states that, for a fixed path length, the absorbance of a solution is proportional to the concentration of the absorbing analyte, which allows us to determine the concentration of an absorbing analyte in an unknown sample.

In hydrocarbon wells, production logging tools often incorporate various sensors, instruments and control devices in order to carry out any number of downhole operations. Thus, the tools may include sensors and/or electronics for formation evaluation, fluid analysis, and so on. Tools that allow testing of fluid properties using instruments located downhole are also known.

SUMMARY OF THE DISCLOSURE

In aspects, the present disclosure is related to methods and apparatuses for evaluating a fluid. Methods may comprise transmitting a light beam through the fluid to a detector while oscillating a path length traveled through the fluid by the light beam at a first frequency of oscillation; measuring a time-dependent intensity of incident light at the detector responsive to an interaction of the light beam with the fluid to produce a time-dependent intensity signal; filtering the time dependent intensity signal to recover a path-dependent signal oscillating at the first frequency and indicative of an absorbance property of the fluid; and estimating a parameter of interest of the fluid using the path-dependent signal. The time-dependent intensity may be indicative of a decrease in intensity between the light beam and the incident light. The time-dependent intensity may be indicative of a difference in intensity caused by absorbance and a difference in intensity caused by non-absorbance related optical effects; and the difference in intensity caused by absorbance may be represented by the path-dependent signal. The difference in intensity caused by non-absorbance related optical effects may be represented by noise in the time-dependent intensity signal.

Methods may include filtering the time-dependent intensity signal using at least one of: i) a band-pass filter centered on a second frequency substantially the same as the first frequency; and ii) a phase-sensitive lock-in amplifier. The fluid may be flowing. The fluid may be a downhole fluid. The fluid may be a highly scattering mixture. The parameter of interest may comprise at least one of: i) an oil fraction of the fluid; ii) a water fraction of the fluid; iii) a gas fraction of the fluid; and iv) a composition of the fluid.

The path length may be oscillated between a minimum path length and a maximum path length; the minimum path length may correspond to a maximum in the path-dependent signal, and the maximum path length may correspond to a minimum in the path-dependent signal. Estimating the parameter of interest may be carried out by using a ratio of a first intensity of the minimum in the path-dependent signal to a second intensity of the maximum in the path-dependent signal to estimate an absorbance of the fluid. The difference between the minimum path length and the maximum path length may be a non-zero value less than one millimeter.

At least one of i) transmitting the light beam through the fluid, and ii) measuring the time-dependent intensity of incident light at the detector, may be carried out using an optical fiber immersed in the fluid. Oscillating the path length may be carried out by moving at least one of a source of the light beam and the detector along a light beam axis with respect to the other of the source and the detector.

Estimating the parameter of interest may be carried out by using spectral information from the incident light. Estimating the parameter of interest may be carried out by estimating an absorbance from the path-dependent signal, and using the absorbance to estimate the parameter of interest.

Apparatus embodiments may include a spectral detector; a light source configured to transmit a light beam through the fluid to the detector; an actuator configured to oscillate a path length traveled through the fluid by the light beam at a first frequency of oscillation; and at least one processor. The at least one processor may be configured to: measure a time-dependent intensity of incident light at the detector responsive to an interaction of the light beam with the fluid to produce a time-dependent intensity signal; filter the time dependent intensity signal to recover a path-dependent signal oscillating at the first frequency and indicative of an absorbance property of the fluid; and estimate a parameter of interest of the fluid using the path-dependent signal.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

Figure 1A:
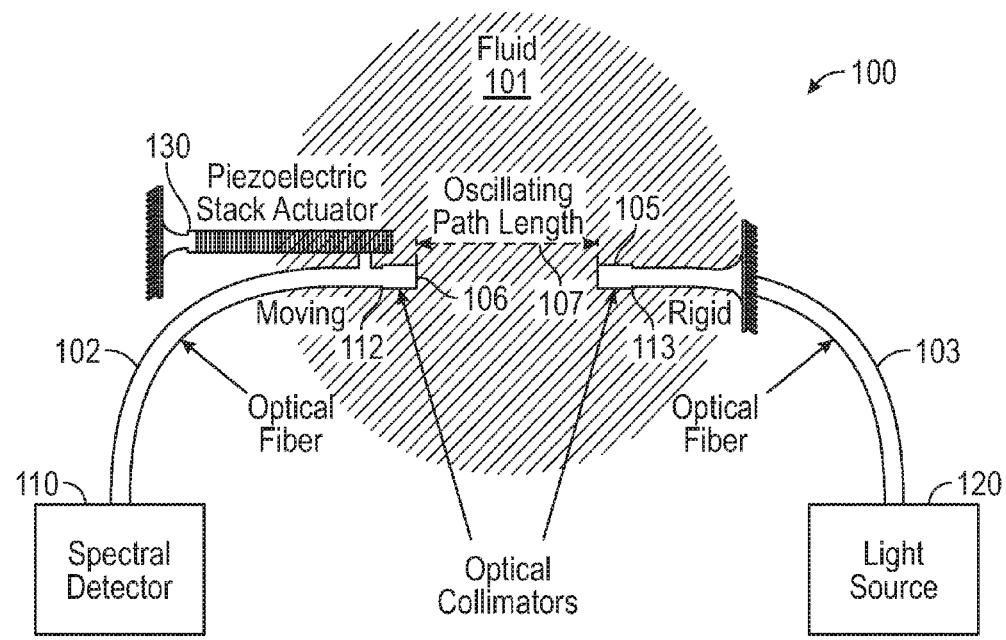
FIG. 1A illustrates an instrument in accordance with embodiments of the present disclosure.

Aspects of the present disclosure relate to apparatus and methods for evaluating a fluid. Aspects are particularly applicable to a flowing fluid with time-varying composition. Results may be estimated in substantially real-time. Aspects of the present disclosure relate to apparatus and methods for downhole logging with respect to fluid evaluation, including measurement and interpretation of physical phenomena indicative of parameters of interest of the formation, the borehole, or the downhole fluids therein.

Techniques described herein are particularly suited to measurement of values of properties of a downhole fluid through the use of instruments utilizing the Beer-Lambert law while mitigating non-absorbance related optical effects (e.g., scattering at the boundaries of fluids of different refractive index) caused by the fluid conditions (e.g., bubbly or frothy immiscible fluid mixtures). These values may be used to evaluate and model the formation or the borehole, and for conducting further operations in the formation or the borehole. See, for example, U.S. Pat. No. 4,664,522 to LeFebre, U.S. Pat. No. 4,786,171 to LeFebre et al., and U.S. Pat. No. 7,826,050 to DiFoggio et al., incorporated herein by reference in its entirety.

Conceptually, for a horizontal sample cell containing static fluids (e.g., head space gas above oil that is floating upon water), a collimated vertical beam of light transmitted through the fluid and detected on the opposite side could be used to quantify the volumetric fractions of each of the respective phases. A decrease in intensity may occur between the transmitted light beam and the incident light, and the resulting absorbance spectra may be compared to the corresponding spectra of a pure sample of each of a group of predicted fluid components.

Over a variety of fields, however, many applications require the light beam of the spectrometer to pass through flowing (rather than static) fluids. Further, the interfaces of the fluids are often not perpendicular to the light beam or to the direction of gravity, and may further be highly variable and may consist of bubbles or slugs of one fluid in another. In some cases, the fluid may contain suspended solid particulates. Each of these factors results in substantial non-absorbance optical effects (e.g., scattering). Any spectroscopic compositional analysis complicated by such scattering, from particulates or multi-phase flow of non-miscible fluids of different refractive indices, becomes problematic. In a typical spectrometer, light aimed in a collimated beam through the fluid towards the detector that does not show up at the detector, is assumed to be absorbed by the fluid when, in fact, that light may simply have been scattered sideways by many intervening interfaces of fluids (or particulates) that have different refractive indices. When the scattering globules are large compared to the wavelength of light, then such scattering can raise the absorbance baseline at all wavelengths by 10 or 20 dB or more, for example, without introducing any wavelength-dependent spectral features. For an intuitive appreciation of the very large effect of scattering, imagine a graduated cylinder filled with ground glass having a refractive index 1.4. It appears white (because all colors are equally scattered) and also opaque much like a shaker of table salt. However, if one now pours in a silicone oil of the same 1.4 refractive index, then the scattering glass-air interfaces will disappear and the graduated cylinder will appear to be simply filled with a transparent liquid.

Aspects of the disclosure include devices, systems and methods for evaluating a fluid, and more particularly a fluid in which transmitted light is subjected to substantial non-absorbance optical effects, such as scattering. Methods of the present disclosure may include transmitting a light beam through the fluid to a detector while oscillating a path length traveled through the fluid by the light beam at a first frequency of oscillation. This may be accomplished by placing the source and/or detector in the fluid, for example, and oscillating the relative position of the two with respect to one another along the direction of the original collimated incident beam ('light beam axis') such that the path length the light travels through the fluid is oscillated. That is, by moving at least one of the source and detector, the source and detector may oscillate towards and then away from one another causing a sinusoidal variation in optical path length within the fluid at substantially (or exactly) the oscillation frequency. By the Beer-Lambert law, absorbance is proportional to path length so, as a result of the path length oscillation, the true absorbance also oscillates at that same frequency.

From experience, for a mixture of immiscible phases that is flowing, a reasonable assumption in this approach is that the attenuation of light caused by scattering is much greater than the attenuation of light caused by true absorption and such scattering attenuation will be observed as an absorbance baseline offset that jumps up and down from one moment to the next (an absorbance baseline "flicker" that depends upon the flow rate, amount of turbulence, and immiscible globule size). For a path length difference of 0.4 millimeters, we can expect the true absorbance difference of gas, oil, or water to be less than 6 db in the wavelength range of 1000 nm to 1850 nm for the methane gas peak at 1667 nm, the liquid oil peak at 1740 nm, and the water peak at 1450 nm. When this assumption is true or when there is no light scattering in the first place, then all of the light reaching the plane of the detector will have the same direction as the original collimated beam path so that moving the detector (or the source) perpendicular to the collimated beam path will cause a sharp drop in the detected light intensity to near zero when the source and detector are no longer aligned within the diameter of the original pencil beam of light. If significant light intensity is detected when source and detector are misaligned by more than the pencil beam of light, then this is a measure of the amount of light scattering and, combined with the aligned light intensity measurement, one can determine both the scattering and the absorption attenuation coefficients using known radiative transfer equations and diffusion theory for photon transport in highly scattering media, such as biological tissue.

The time-dependent intensity of incident light (responsive to an interaction of the light beam with the fluid) may be measured at the detector to produce a time-dependent intensity signal. When the above assumption is true, then the time-dependent intensity signal may be indicative of a difference in intensity caused by true absorbance at the minimum and at the maximum path lengths. Specifically, the true absorbance associated with the path length difference (maximum path length–minimum path length) equals the base ten logarithm of the ratio of the maximum light intensity to the minimum light intensity of this time dependent signal. Signal recovery with this oscillating path length method is aided by AC filtering that only allows that portion of the signal at the oscillation frequency to be considered. Further signal recovery enhancement can be achieved by filtering not only by frequency but also by the phase of the oscillation as one can do with a lock in amplifier, which may be needed when the absorbance baseline "flicker" is at a frequency that is comparable to the oscillating path length frequency. Preferably, the instrument should be designed with a dynamic range that is at least 10 db greater than the maximum scattering attenuation for the maximum path length to insure that a small AC signal at the oscillation frequency can be recovered from a large, flickering, DC offset.

FIG. 1A illustrates an instrument in accordance with embodiments of the present disclosure. The instrument 100 comprises two optical fibers (102, 103) immersed in the fluid 101, and each terminated at an end 112, 113, respectively, with an optical collimator (104, 105).

The fluid 101 may be a moving fluid interior or exterior to a device housing (not shown) associated with the instrument. One of the fibers 103 is operatively optically coupled to a light source 120. Another of the fibers 102 is operatively optically coupled to a spectral detector 110.

Absorbance spectra of fluids may be collected over a small gap, such as, for example, 0.5-5.0 millimeters, and preferably 0.6-1.0 mm, between the two immersed optical fibers. One of the fibers 102 may oscillate towards and then away from the other, causing a sinusoidal variation in optical path length at substantially (or exactly) the oscillation frequency. The movement of the fiber 102 thus creates a time-varying path length 107 which oscillates between a minimum path length and a maximum path length. In one example, the gap may be approximately 1 millimeter, and the difference between the minimum and the maximum may be approximately 0.4 millimeters.

The movement of the fiber(s) causing the oscillation of path length may be implemented using a piezoelectric stack actuator 130, such as Flextensional Piezo Actuators commercially available from Dynamic Structures & Materials of Franklin, Tenn. In other implementations, to maintain better fiber alignment, a more symmetric design may be employed using a hollow piezoelectric stack, with the fiber attached to the inside of this stack so as to move one fiber relative to the other. Additional sensors may be used to independently confirm (via measurement) the movement of the fiber end, and thus the time varying path length exact phase and frequency.

For a conventional rigid downhole fluid sample cell, the window separation distance is fixed and, even if redesigned to permit variation, increasing that distance may require working against a very large hydrostatic pressure, which would be difficult by itself and unrealistic at any rapid rate of separation variation as is proposed here. One advantage of an immersed optical fiber system is that separation distance between immersed fibers can be changed by simply flexing at least one immersed fiber while avoiding work against hydrostatic pressure.

An earlier patent, U.S. Pat. No. 8,145,064 to Majewski et al., is for a spectrometer, and has the phrase "path length modulation" in it. However, Majewski is about changing the "optical pathlength" (meaning the refractive index multiplied by physical length) of each of two optical fibers 41 (one, whose light is going to the sample, and the other, whose light is returning from the sample). Majewski is not about changing the pathlength 28 of the sample, itself, and its purpose is to do dithering for noise reduction rather than actually modulating the optical absorbance of the sample by oscillating the sample's pathlength as in the current disclosure.

Majewski's disclosure of a "path length modulation" frequency of 15 MHz to 30 MHz is conclusive proof that path length is not being modulated, as modulation of sample path length at such a high frequency is not feasible. Only the so-called "optical path length" (refractive index multiplied by physical path length) of the light traveling within an optical fiber could be changed that fast with a piezoelectric actuator (Col 8 Line 44) in order to stretch or relax the fiber, and thereby slightly change its refractive index.

Figure 2:
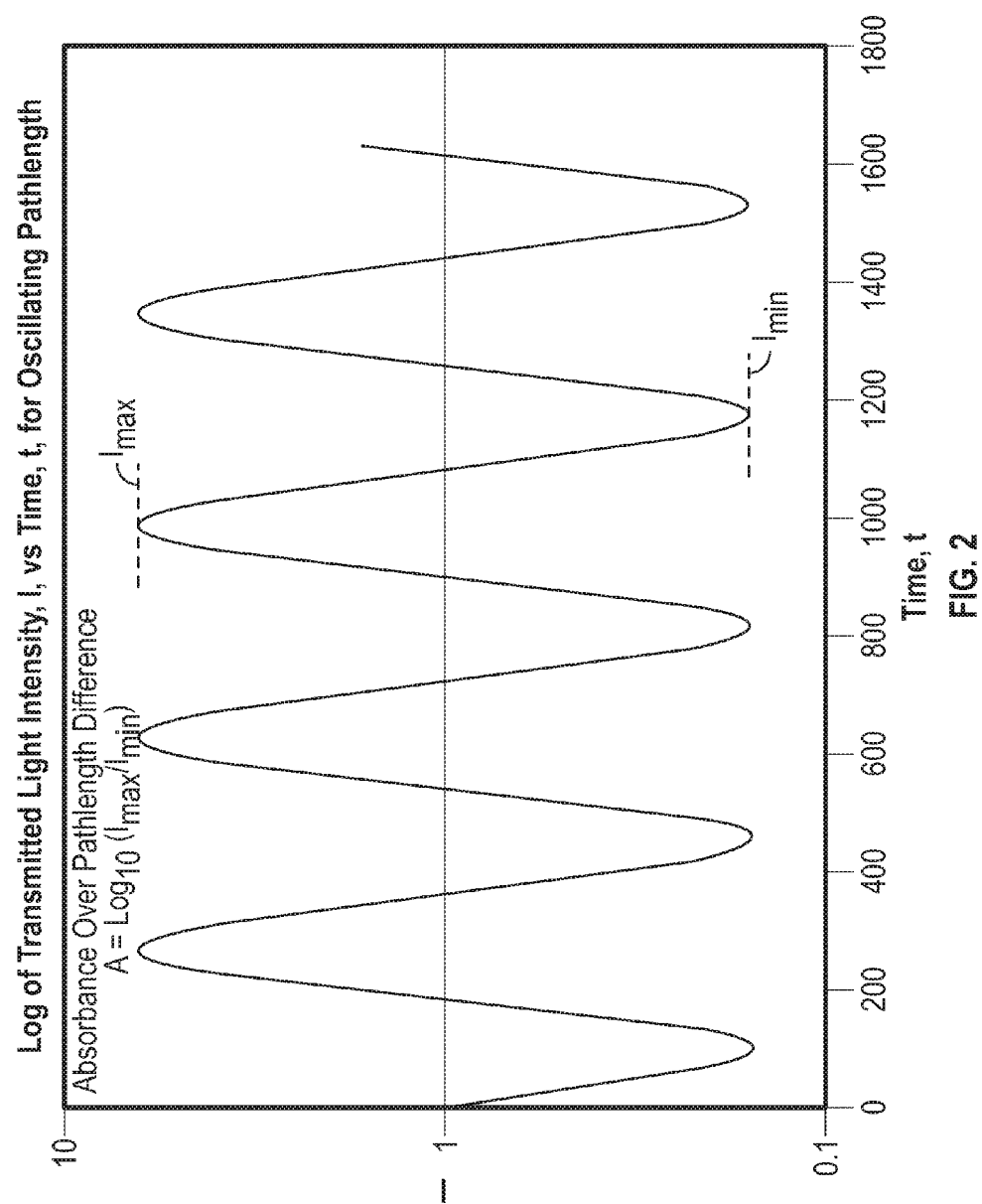
FIG. 2 illustrates the oscillation of intensity over time due to path length oscillation.

FIG. 2 illustrates the oscillation of intensity over time due to path length oscillation. The absorptivity ($\alpha$) of the absorber may be expressed as $$\alpha = (\text{Absorbance/Unit\_Length})$$

at 100% concentration of absorber (c).

Because $$L = L_0 \sin(\omega t),$$

the optical path length difference (subtracting the minimum path length in the fluid from the maximum path length in the fluid) is $2 L_0$, because $\sin(\omega t)$ ranges −1 to +1. The base ten logarithm of a ratio of the (brighter) light transmitted through the shortest path length to the (dimmer) light transmitted through the longest path length is the optical absorbance for the maximum path length difference of $2 L_0$. Responsive to an incident light intensity ($I_0$), the transmitted light intensity (I), in accordance with Beer's Law, may be expressed as $$I = I_0 10^{-\alpha c L} = I_0 10^{-\alpha L_0 \sin(\omega t)}$$

The optical absorbance (A) is equal to $$A = \text{Log}_{10}(I_0/I) = \alpha c L_0 \sin(\omega t)$$

For the oscillating path length method, one does not need $I_0$ but only the ratio of the maximum to minimum light intensity that is measured. That is, the absorbance, A, for a path length equal to the maximum oscillating path length difference, is given by, $$A = \text{Log}_{10}(I_{max}/I_{min})$$

Thus, while using system 100 to generate a time-dependent intensity signal, the true absorbance is oscillating at the same frequency as the oscillating path length in the fluid (L), which allows the true absorbance to be distinguished from any scattering effects by using filtering, such as, for example, a narrow bandpass digital filter at the oscillation frequency. Greater advantage may be obtained, in some applications, by using a frequency and phase-sensitive lock-in amplifier implementation, which detects a response at a reference frequency.

Phase-sensitive synchronous detection is an advantageous technique for the recovery of minute signals which may be obscured by noise which is much larger than the signal of interest. Lock-in amplifiers may be used to detect and measure very small alternating current ('AC') signals of an amplitude on the scale of $10^{-9}$ volts, and make possible accurate measurements of a signal obscured by noise sources many thousands of times larger. Lock-in amplifiers may use a technique known as phase-sensitive detection to isolate the component of the signal at a specific reference frequency and phase. Noise signals, at frequencies other than the reference frequency, are rejected.

Figure 1B:
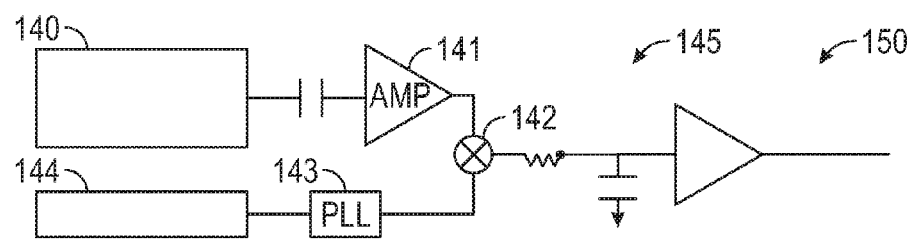
FIG. 1B illustrates a lock-in amplifier in accordance with embodiments of the present disclosure.
Figure 1C:
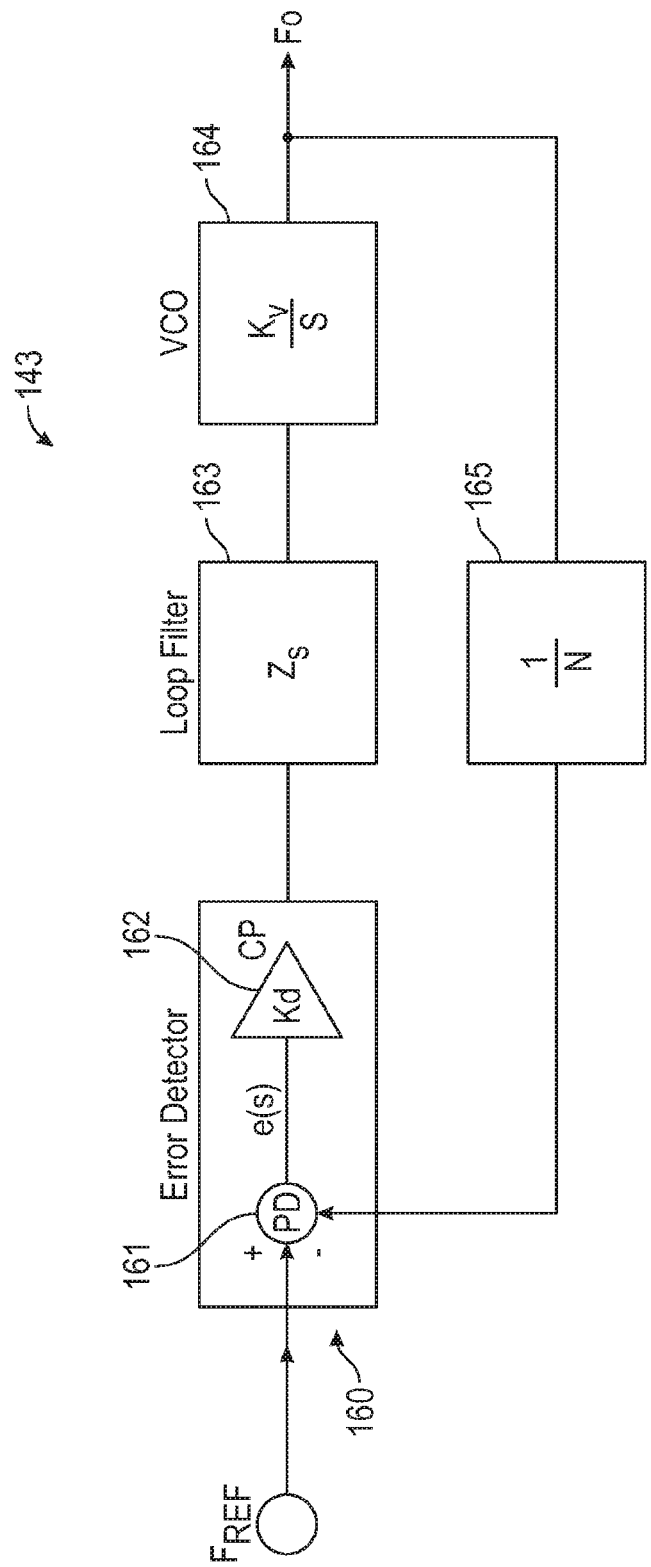
FIG. 1C illustrates a phase locked loop in accordance with embodiments of the present disclosure.

FIG. 1B illustrates a lock-in amplifier in accordance with embodiments of the present disclosure. FIG. 1C illustrates a phase locked loop in accordance with embodiments of the present disclosure. In the amplifier 150 of FIG. 2, the voltage signal 140 generated by the first stage of the spectral detector in response to the optical signal received via the fiber 102 may be AC-coupled to an amplifier 141. Phase sensitive detection operates by modeling the signal as $\cos(\omega_1 t)$ and the reference frequency as $\cos(\omega_1 t + \Phi)$, where $\Phi$ is the phase shift. Using a mixer 142, the output of the amplifier 141 is multiplied by the output of a phase-locked loop 143 which is locked to a generated reference input 144 matching the physical oscillation frequency for the path length. The operation of the mixer 142 may be understood through the trigonometric identity $$\cos(\omega_1 t+\Phi)*\cos(\omega_2 t)=\tfrac{1}{2}[\cos((\omega_1+\omega_2)t+\Phi)+\cos((\omega_1-\omega_2)t+\Phi)].$$

When $\omega_1=\omega_2$ there is a direct current ('DC') component of the mixer output, cos ($\Phi$). The output of the mixer 142 may be passed through a low-pass filter 145 to remove the sum frequency component. Lock-in amplifier 150 measures the component of the signal at one phase with respect to the reference. Signal frequencies close to the reference frequency for a low frequency beat. The beat frequency approaches DC as the signal frequency approaches the reference frequency. The DC output may depend on relative phase. In some instances, detection occurs only at the modulation frequency, while noise at other frequencies averages to zero.

Phase-locked loop 143 is made up of an Error Detector 160 comprising a phase frequency detector 161 and a charge pump 162, Loop Filter 163, VCO 164, and a Feedback Divider 165. Negative feedback forces the error signal, e(s), to approach zero at which point the feedback divider output and the reference frequency are in phase and frequency lock, and $F_O=N_{FREF}$. See for example, Tutorial MT-086, Phase Locked Loops. *Analog Devices.*

Embodiments may implement filters using one or more Digital Signal Processors ('DSPs'). DSP implementations may digitize in the input using a high-speed analog-to-digital converter ('ADC'). The digital signal's amplitude and phase may be determined by high-speed computations in a DSP.

For example, the spectral detector may include a digital lock-in amplifier (DLIA), such as the SR850 model DSP lock-in amplifier commercially available from Stanford Instruments. See also, for example, Cheng et al. A Digital Lock-In Amplifier for Use at Temperatures of up to 200 degrees Celsius. Sensors 2016, 16, 1899; doi:10.3390/s16111899, at URL: <<http://www.mdpi.com/journal/sensors>>. Cheng describes the use of MCU (TMS320F2812) and FPGA (A3P1000) chip wafers suitable for use in high temperatures, along with other Silicon-On-Insulator (SOI) chip wafers, provided by Xi'an Microelectronics (Xi'an, China) combined in a high-temperature system-in-package (SiP), operating with a digital lock-in amplifier algorithm.

In aspects, this disclosure relates to making a downhole measurement. Downhole measurement, as used herein, may be defined as a measurement taken in a borehole intersecting an earth formation indicative of a parameter of interest of the borehole, the formation, or a fluid therein, i.e., a downhole parameter. Aspects of the present disclosure relate to fluid analysis. Techniques described herein are particularly suited to measurement of values of properties of a downhole fluid through the use of instruments utilizing physical phenomena. These values may be used to evaluate and model the formation or the borehole, and for conducting further operations in the formation or the borehole.

Aspects of the present disclosure relate to modeling a volume of an earth formation. The model of the earth formation generated and maintained in aspects of the disclosure may be implemented as a representation of the earth formation stored as information. The information (e.g., data) may be stored on a non-transitory machine-readable medium, transmitted, and rendered (e.g., visually depicted) on a display.

The present disclosure is susceptible to embodiments of different forms. There are shown in the drawings, and herein will be described in detail, specific embodiments of the present disclosure with the understanding that the present disclosure is to be considered an exemplification of the principles of the disclosure, and is not intended to limit the disclosure to that illustrated and described herein. Indeed, as will become apparent, the teachings of the present disclosure can be utilized for a variety of well tools and in all phases of well construction and production. Accordingly, the embodiments discussed below are merely illustrative of the applications of the present disclosure.

As described herein, aspects of the disclosure include systems and techniques for spectroscopically conducted component analysis of a fluid where the fluid phases are rapidly changing in time and scattering causes rapid absorbance baseline rises, which can overwhelm the true spectra. In some implementations, such systems and techniques may be used for measuring gas, oil, and water fractions with a production logging tool. Of course, these techniques could also be used to collect spectra during sampling either on wireline or as part of logging-while-drilling or measurement-while-drilling.

Figure 3:
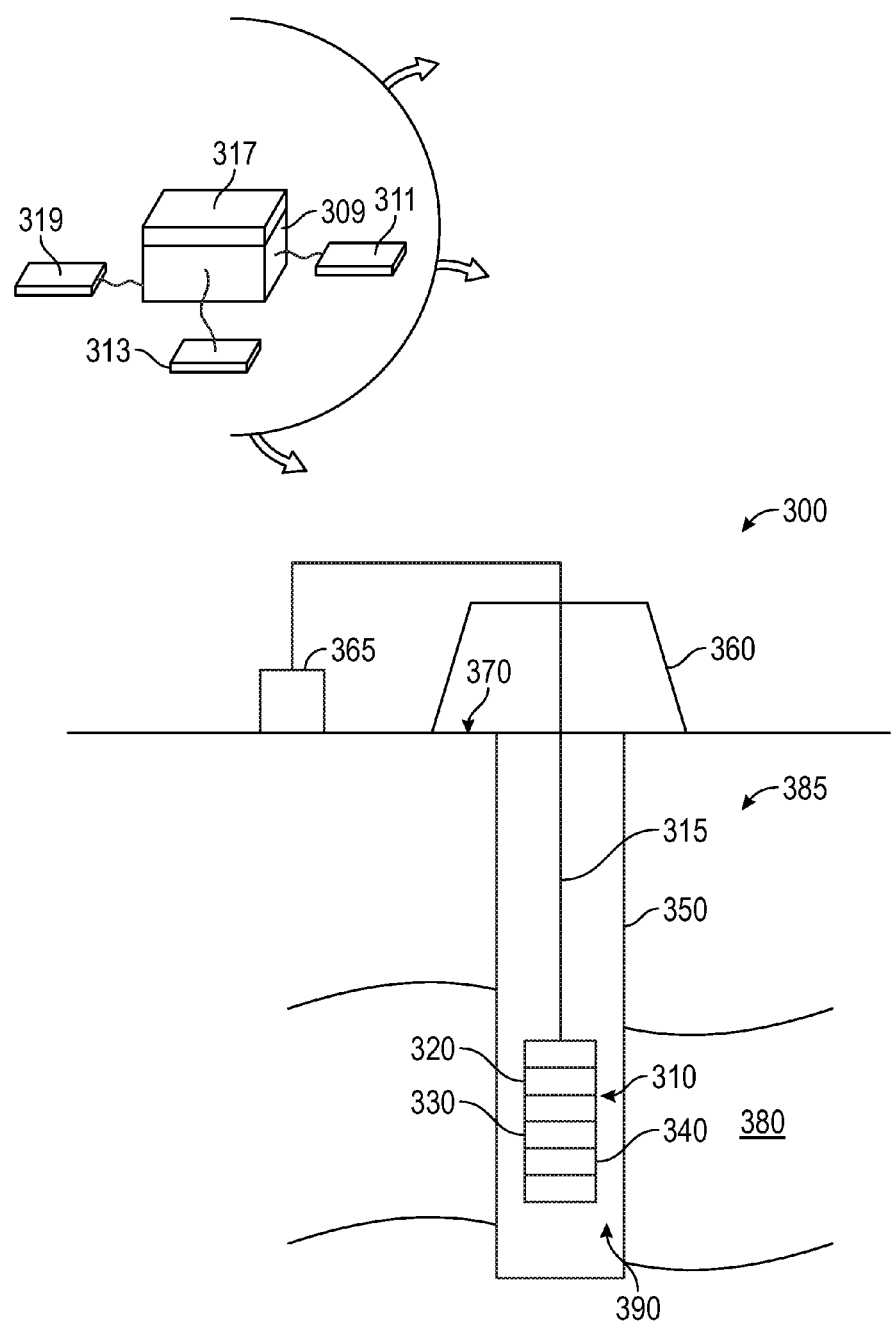
FIG. 3 schematically illustrates a system having a downhole tool configured to acquire information for estimating a downhole parameter of interest in accordance with embodiments of the present disclosure.

FIG. 3 schematically illustrates a system 300 having a downhole tool 310 configured to acquire information for estimating a downhole parameter of interest (e.g., a value of a property of the formation 380, the borehole 350, or downhole fluid 390 therein) using instrument 340. Aspects of the present disclosure are subject to application in various different embodiments. In some general embodiments, carrier 315 is implemented as a tool string of a drilling system, and measurements taken in the borehole may be characterized as "logging-while-drilling" (LWD) or "measurement-while-drilling" (MWD) operations.

The system 300 may include a conventional derrick 360 erected on a derrick floor 370. A conveyance device (carrier 315) which may be rigid or non-rigid, may be configured to convey the downhole tool 310 into wellbore 350 in proximity to a volume of interest 380 of an earth formation 385. The carrier 315 may be a drill string, coiled tubing, a slickline, an e-line, a wireline, etc. Downhole tool 310 may be coupled or combined with additional tools e.g., some or all the information processing system (inset). Thus, depending on the configuration, the tool 310 may be used during drilling and/or after the wellbore 350 has been formed. As described herein, "borehole" or "wellbore" refers to a single hole that makes up all or part of a drilled well. While a land system is shown, the teachings of the present disclosure may also be utilized in offshore or subsea applications. The carrier 315 may include embedded conductors for power and/or data for providing signal and/or power communication between the surface and downhole equipment (e.g., a seven conductor cable). The carrier 315 may include a bottom hole assembly, which may include a drilling motor for rotating a drill bit.

An instrument as described above is configured to be conveyed in a borehole on tool 310 and to measure a parameter of interest. In some embodiments, the instrument may include a surface in contact with the borehole fluid, and some (or all) of the instrument may protrude from the tool body into the borehole. In other embodiments, the tool may include a fluid testing channel through which the fluid is conveyed.

Tool 310 may include circuitry for making measurements using the instrument 340. Circuitry may include a control unit operatively connected to spectral detector 110 and light source 120 as well as provide power to operate the piezoelectric stack actuator. Circuitry may be implemented as at least one processor described below or may be an additional processor or other supporting circuitry. The detector may be implemented as a spectrometer or other spectrographic detector including a mechanism for separating light into component wavelengths and a detector for sensing the intensity at each wavelength.

Downhole fluid (e.g., drilling fluid, or 'mud') 390 may be present between the formation 385 and the downhole tool 310. A surface control system 365 receives signals from instrument(s) 340 or electronics 330 indicative of measurements of the downhole fluid 390 and other sensors used in the system 300 and processes such signals according to programmed instructions provided to the surface control system 365. The surface control system 365 may display desired parameters and other information on a display/monitor that is utilized by an operator. The surface control system 365 may further communicate with a downhole control system 320 at a suitable location on downhole tool 310. The surface control system 365 may process data relating to the operations and data from the instrument 340, and may control one or more downhole operations performed by system 300.

In one embodiment, electronics 330 associated with instrument 340 may be configured to record and/or process the information obtained. Certain embodiments of the present disclosure may be implemented with a hardware environment that includes an information processor 317, an information storage medium 313, an input device 311, processor memory 309, and may include peripheral information storage medium 319. The hardware environment may be in the well, at the rig, or at a remote location. Moreover, the several components of the hardware environment may be distributed among those locations. The input device 311 may be any data reader or user input device, such as data card reader, keyboard, USB port, etc. The information storage medium 313 stores information provided by the detectors. Information storage medium 313 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 313 stores a program that when executed causes information processor 317 to execute the disclosed method. Information storage medium 313 may also store the formation information provided by the user, or the formation information may be stored in a peripheral information storage medium 319, which may be any standard computer information storage device, such as a USB drive, memory stick, hard disk, removable RAM, or other commonly used memory storage system known to one of ordinary skill in the art including Internet based storage. Information processor 317 may be any form of computer or mathematical processing hardware, including Internet based hardware. When the program is loaded from information storage medium 313 into processor memory 309 (e.g. computer RAM), the program, when executed, causes information processor 317 to retrieve detector information from either information storage medium 313 or peripheral information storage medium 319 and process the information to estimate a parameter of interest. Information processor 317 may be located on the surface or downhole.

Therefore, processors may include an information processor that is in data communication with a data storage medium and a processor memory. The data storage medium may be any standard computer data storage device, such as a USB drive, memory stick, hard disk, removable RAM, EPROMs, EAROMs, flash memories and optical disks or other commonly used memory storage system known to one of ordinary skill in the art including Internet based storage. The data storage medium may store one or more programs that when executed causes information processor to execute the disclosed method(s).

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

To perform the analysis during a single trip, the tool may use a high bandwidth transmission to transmit the information acquired by electronics 330 via instrument 340 to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "substantially real-time."

One point of novelty of the system illustrated in FIG. 3 is that the surface control system 365 and/or the downhole control system 320 are configured to perform certain methods (discussed below) that are not in the prior art. A surface control system or downhole control system may be configured to control the tool described above and any incorporated sensors and to estimate a parameter of interest according to methods described herein. In one embodiment, electronics (not shown) associated with the sensors may be configured to record information related to the parameters to be estimated. In some embodiments, the parameter of interest may be estimated using the recorded information.

A surface control unit and/or downhole control unit may be configured to control sensors described above and to estimate a parameter of interest according to methods described herein. Control of these components may be carried out using one or more models or algorithms using methods described below. Mathematical models, look-up tables, or other models representing relationships between the signals and the values of the formation properties may be used to characterize operations in the formation or the formation itself, optimize one or more operational parameters of a production or development, and so on. The system may carry out these actions through notifications, advice, and/or intelligent control.

Figure 4:
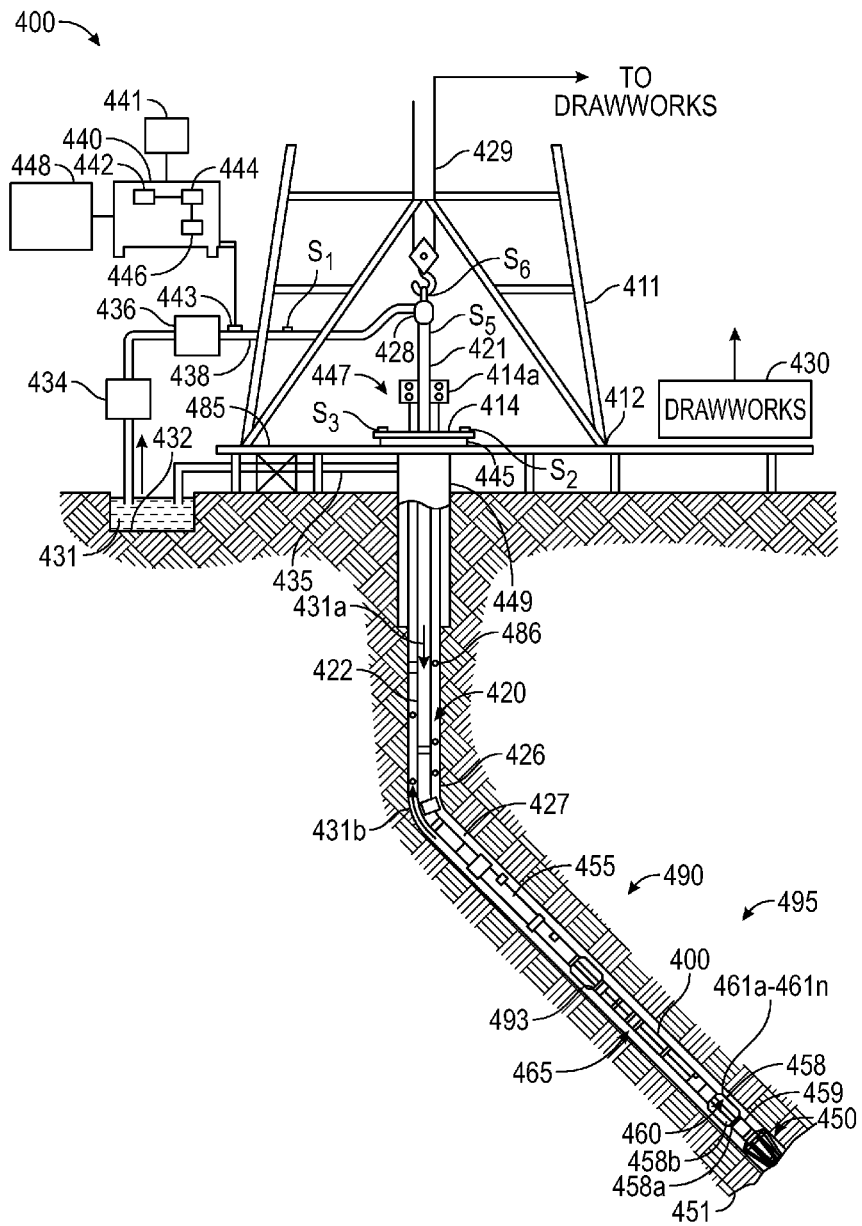
FIG. 4 shows an example embodiment of an MWD system for downhole evaluation in accordance with embodiments of the present disclosure.

FIG. 4 shows an example embodiment of an MWD system for downhole evaluation using spectroscopic analysis. The system 401 includes a carrier 411 that is shown disposed in a wellbore or borehole 426 that penetrates at least one earth formation 495. The system 401 also includes a tool 410 configured for conducting fluid analysis in the borehole as disclosed herein.

FIG. 4 shows a drill string 420 including a bottomhole assembly (BHA) 490 conveyed in the borehole 426 as the carrier. The drilling system 401 includes a conventional derrick 411 erected on a platform or floor 412 which supports a rotary table 414 that is rotated by a prime mover, such as an electric motor (not shown), at a desired rotational speed. A tubing (such as jointed drill pipe 422), having the drilling assembly 490, attached at its bottom end extends from the surface to the bottom 451 of the borehole 426. A drill bit 450, attached to drilling assembly 490, disintegrates the geological formations when it is rotated to drill the borehole 426. The drill string 420 is coupled to a drawworks 430 via a Kelly joint 421, swivel 428 and line 429 through a pulley. Drawworks 430 is operated to control the weight on bit ("WOB"). The drill string 420 may be rotated by a top drive (not shown) instead of by the prime mover and the rotary table 414. Alternatively, a coiled-tubing may be used as the tubing 422. A tubing injector 414a may be used to convey the coiled-tubing having the drilling assembly attached to its bottom end. The operations of the drawworks 430 and the tubing injector 414a are known in the art and are thus not described in detail herein.

It should be understood that embodiments of the present disclosure are well suited for use in wells having various configurations including horizontal wells, deviated wells, slanted wells, multilateral wells and so on. Accordingly, use of directional terms herein (e.g., above, below, upper, lower, upward, downward, topmost, lowermost, uphole, downhole, etc) refer to the direction of travel along the borehole either toward or away from the surface, with the upward direction being toward the surface and the downward direction being away from the surface.

A suitable drilling fluid 431 (also referred to as the "mud") from a source 432 thereof, such as a mud pit, is circulated under pressure through the drill string 420 by a mud pump 434. The drilling fluid 431 passes from the mud pump 434 into the drill string 420 via a discharger 436 and the fluid line 438. The drilling fluid 431a from the drilling tubular discharges at the borehole bottom 451 through openings in the drill bit 450. The returning drilling fluid 431b circulates uphole through the annular space 427 between the drill string 420 and the borehole 426 and returns to the mud pit 432 via a return line 435 and drill cutting screen 485 that removes the drill cuttings 486 from the returning drilling fluid 431b. A sensor S1 in line 438 provides information about the fluid flow rate. A surface torque sensor S2 and a sensor S3 associated with the drill string 420 respectively provide information about the torque and the rotational speed of the drill string 420. Tubing injection speed is determined from the sensor S5, while the sensor S6 provides the hook load of the drill string 420.

Well control system 447 is placed at the top end of the borehole 426. The well control system 447 includes a surface blow-out-preventer (BOP) stack 415 and a surface choke 449 in communication with a wellbore annulus 427. The surface choke 449 can control the flow of fluid out of the borehole 426 to provide a back pressure as needed to control the well.

In some applications, the drill bit 450 is rotated by only rotating the drill pipe 422. However, in many other applications, a downhole motor 455 (mud motor) disposed in the BHA 490 also rotates the drill bit 450. The rate of penetration (ROP) for a given BHA largely depends on the WOB or the thrust force on the drill bit 450 and its rotational speed.

A surface control unit or controller 440 receives signals from the downhole sensors and devices via a sensor 443 placed in the fluid line 438 and signals from sensors S1-S6 and other sensors used in the system 401 and processes such signals according to programmed instructions provided to the surface control unit 440. The surface control unit 440 displays drilling parameters and other parameters of interest related to the borehole, formation, and drilling operations, and other information on a display/monitor 441 that is utilized by an operator to control the drilling operations. The surface control unit 440 may be a computer-based unit that may include a processor 442 (such as a microprocessor), a storage device 444, such as a solid-state memory, tape or hard disc, and one or more computer programs 446 in the storage device 444 that are accessible to the processor 442 for executing instructions contained in such programs. The surface control unit 440 may further communicate with a remote control unit 448. The surface control unit 440 may process data relating to the drilling operations, data from the sensors and devices on the surface, and data received from downhole; and may control one or more operations of the downhole and surface devices. The data may be transmitted in analog or digital form.

The BHA 490 may include a tool 410 configured for performing spectroscopic fluid analysis downhole. The BHA 490 may also contain other formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 495 surrounding the BHA 450. For convenience, all such sensors are generally denoted herein by numeral 465. The BHA 490 may further include a variety of other sensors and devices 459 for determining one or more properties of the BHA 490, such as vibration, bending moment, acceleration, oscillations, whirl, stick-slip, weight-on-bit, fluid flow rate, pressure, temperature, rate of penetration, azimuth, tool face, drill bit rotation, etc.

The BHA 490 may include a steering apparatus or tool 458 for steering the drill bit 450 along a desired drilling path. In one aspect, the steering apparatus may include a steering unit 460, having a number of force application members 461a-461n. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 458 having a bent sub and a first steering device 458a to orient the bent sub in the wellbore and the second steering device 458b to maintain the bent sub along a selected drilling direction. The steering unit 458, 460 may include near-bit inclinometers and magnetometers.

The drilling system 401 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 420 to provide the required force on the drill bit.

Example sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 401 can include one or more downhole processors at a suitable location such as 493 on the BHA 490. The processor(s) can be a microprocessor that uses a computer program implemented on a suitable non-transitory computer-readable medium that enables the processor to perform the control of system 401 and processing of information, such as information from the sensors. The non-transitory computer-readable medium may include one or more ROMs, EPROMs, EAROMs, EEPROMs, flash memories, RAMs, hard drives and/or optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 442 can process at the surface measured data, along with the data transmitted from the downhole processor, to evaluate the formation.

Surface processor 442 or downhole processor 493 may also be configured to control steering apparatus 458, mud pump 434, drawworks 430, rotary table 414, downhole motor 455, other components of the BHA 490, or other components of the drilling system 401. Surface processor 442 or downhole processor 493 may be configured to control spectroscopic fluid analysis instruments as described above and to estimate a parameter of interest according to methods described herein.

Control of these components may be carried out using one or more models using methods described below. For example, surface processor 442 or downhole processor 493 may be configured to modify drilling operations i) autonomously upon triggering conditions, ii) in response to operator commands, or iii) combinations of these. Such modifications may include changing drilling parameters, steering the drillbit (e.g., geosteering), altering the drilling fluid program, activating well control measures, and so on. Control of these devices, and of the various processes of the drilling system generally, may be carried out in a completely automated fashion or through interaction with personnel via notifications, graphical representations, user interfaces and the like. Reference information accessible to the processor may also be used. In some general embodiments, surface processor 442, downhole processor 493, or other processors (e.g. remote processors) may be configured to operate the fluid analysis tool.

The system 401 may include any number of downhole tools for various processes including formation drilling, geosteering, and formation evaluation (FE) for making electrical measurements versus depth and/or time of one or more physical properties in or around a borehole, including a volume of interest of the formation intersected by the borehole.

Figure 5:
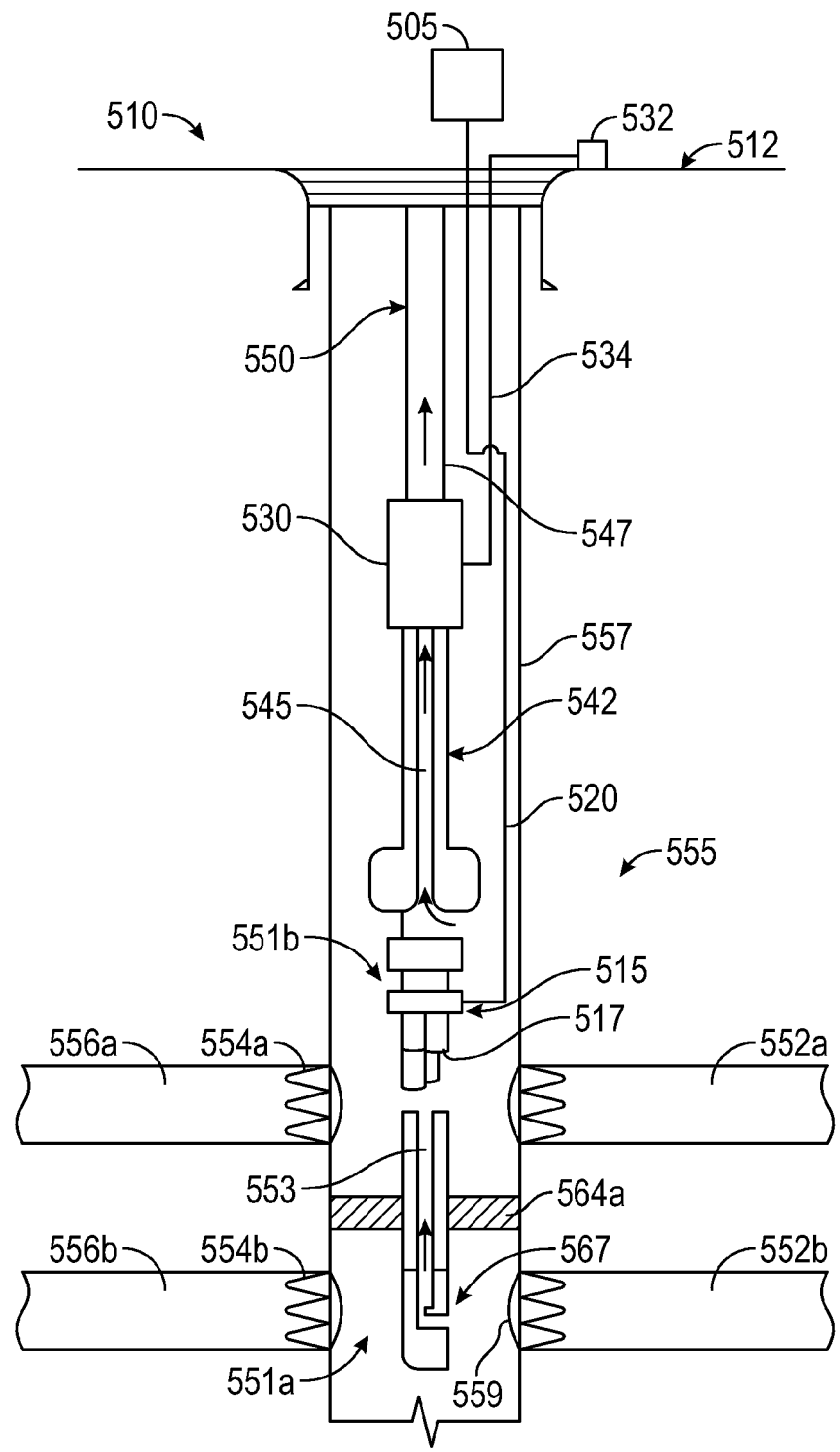
FIG. 5 shows a schematic illustration of a production system including a device in accordance with embodiments of the present disclosure.

FIG. 5 shows a schematic illustration of a production system including a device in accordance with embodiments of the present disclosure. FIG. 5 shows a well 550 that produces formation fluids 556a and 556b including hydrocarbons from two exemplary production zones, 552a (upper production zone) and 552b (lower production zone), respectively, in a formation 555. Casing 557 lines the well. Perforations 554a adjacent the upper production zone 552a and perforations 554b adjacent the lower production zone 552b facilitate recovery of formation fluids. A packer 564a positioned above (uphole) of the lower production zone perforations 554a isolates the lower production zone 552b from the upper production zone 552a. A screen 555 inhibiting solids, such as sand, from entering into the wellbore may be installed adjacent the perforations.

The formation fluid 556b from the lower production zone 552b enters the annulus 551a of the well 550 through the perforations 554a and into a tubing 553 via a flow control valve 567. The formation fluid 556a from the upper production zone 552a enters the annulus 551b (the annulus portion above the packer 564a) via perforations 554a. The formation fluid 556a enters production tubing or line 545 via inlets 542.

In cases where the formation pressure is not sufficient to push the fluid 556a and/or fluid 556b to the surface, an artificial lift mechanism, such as an electrical submersible pump (ESP) or other lift system may be utilized to lift the fluids from the well to the surface 512. ESP 530 receives formation fluids 556a and 556b and pumps the fluids via tubing 547 to the surface 512. Two-way data communication may be provided between ESP 530 and ESP control unit 532 by cable 534. ESP control unit 532 may control the operation of ESP 530. ESP control unit 532 may include a processor configured to analyze and control the operations of ESP 530. ESP control unit 532 may be configured to alter pump speed of the ESP by sending control signals in response to data or instructions received from another controller.

Data communication lines run inside the well 550 to operate the various devices in the well 550 and to obtain measurements and other data from the various sensors in the well 550. A variety of other sensors may be placed at suitable locations in the well 550 to provide measurements or information relating to a number of downhole parameters of interest.

One or more gauge or sensor carriers, such as a carrier 515, may be placed in the production tubing to house any number of suitable sensors and/or instruments, including fluid analysis instruments as disclosed herein, or components thereof. The carrier 515 includes permanent well monitoring sensor 517 comprising instrument 100 for estimating characteristics of the production fluid. Data communication line 547 may transmit data from permanent well monitoring sensor 517 to well controller 505 at the surface 512. Well controller 505 may include electrical circuitry configured to control one or more components of the system 500. In other embodiments, controller 505 may be implemented in a hardware environment as described below, and use algorithms and programming to receive information and control operation of the production system 500, such as for example, controlling ESP 530.

Figure 6:
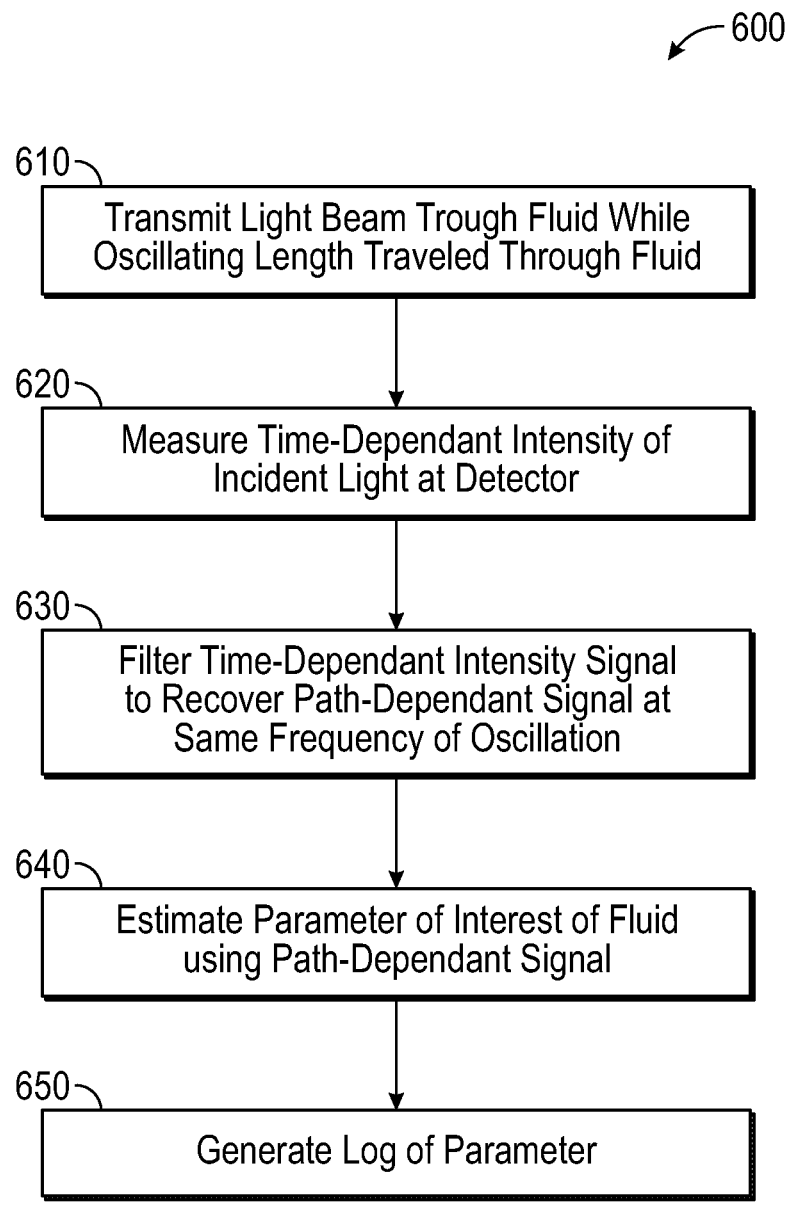
FIG. 6 shows a flow chart illustrating methods for evaluating a fluid in accordance with embodiments of the present disclosure.

FIG. 6 shows a flow chart 600 illustrating methods for evaluating a fluid in accordance with embodiments of the present disclosure. Step 610 comprises transmitting a light beam through the fluid to a detector while oscillating a path length traveled through the fluid by the light beam at a first frequency of oscillation. The fluid may be a highly scattering mixture. Oscillating the path length may be carried out by moving at least one of a source of the light beam and the detector with respect to the other of the source and the detector.

Step 620 comprises measuring a time-dependent intensity of incident light at the detector responsive to an interaction of the light beam with the fluid to produce a time-dependent intensity signal. At least one of i) transmitting the light beam through the fluid, and ii) measuring the time-dependent intensity of incident light at the detector, may be carried out using an optical fiber immersed in the fluid. The time-dependent intensity may be indicative of a decrease in intensity between the light beam and the incident light.

The path length is oscillated between a minimum path length and a maximum path length; the minimum path length corresponds to a maximum in the path-dependent signal, and the maximum path length corresponds to a minimum in the path-dependent signal.

Step 630 comprises filtering the time-dependent intensity signal to recover a path-dependent signal oscillating at the first frequency and indicative of an absorbance property of the fluid. Step 630 may be carried out by filtering the time-dependent intensity signal using at least one of: i) a band-pass filter centered on a second frequency substantially the same as the first frequency; and ii) a phase-sensitive lock-in amplifier.

Step 640 comprises estimating a parameter of interest of the fluid using the path-dependent signal. Step 640 may be carried out by using a ratio of a first intensity of the minimum in the path-dependent signal to a second intensity of the maximum in the path-dependent signal to estimate an absorbance of the fluid at the various wavelengths at which the different analytes (oil, water, gas) absorb. In some cases, the absorbance may be used to estimate the parameter of interest. Step 640 may include estimating the parameter of interest using spectral information from the incident light. For example, step 640 may include using spectral lines to determine the component composition of the corresponding respective concentrations in the sample. Step 640 may be carried out by deconvolving a response spectrum from the path-dependent signal embodied by the spectral information into a plurality of component spectral yields. Methods may include deconvolving the spectrum using one or more separately determined standard spectra. The parameter of interest may comprise at least one of: i) an oil fraction of the fluid; ii) a water fraction of the fluid; iii) a gas fraction of the fluid; and iv) a composition of the fluid.

In additional optional steps, a fluid analysis instrument may be conveyed in a borehole using a carrier. The borehole is filled with downhole fluid which may be non-transparent. The estimation may be performed in multiple stages, such that an earlier stage may process the information for a later stage. The term "response spectrum" refers to not only the response spectrum as originally acquired, but also after filtering, corrections, or pre-processing is applied.

Estimation of the parameter may include the use of a model. In some embodiments, the model may include, but is not limited to, one or more of: (i) a mathematical equation, (ii) an algorithm, (iii) an deconvolution technique, and so on. Reference information accessible to the processor may also be used.

Optional step 650 comprises generating a log of the spectral information. Other optional steps may include performing at least one of: i) storing the log on a on a non-transitory machine-readable medium; and ii) transmitting the log to another processor. Herein, "information" may include raw data, processed data, analog signals, and digital signals.

Estimated parameters of interest may be stored (recorded) as information or visually depicted on a display. The parameters of interest may be transmitted before or after storage or display. For example, information may be transmitted to other downhole components or to the surface for storage, display, or further processing. Aspects of the present disclosure relate to modeling a volume of an earth formation using the estimated parameter of interest, such as, for example, by associating estimated parameter values with portions of the volume of interest to which they correspond. The model of the earth formation generated and maintained in aspects of the disclosure may be implemented as a representation of the earth formation stored as information. The information (e.g., data) may also be transmitted, stored on a non-transitory machine-readable medium, and/or rendered (e.g., visually depicted) on a display.

The processing of the measurements by a processor may occur at the tool, the surface, or at a remote location. The data acquisition may be controlled at least in part by the electronics. Implicit in the control and processing of the data is the use of a computer program on a suitable non-transitory machine readable medium that enables the processors to perform the control and processing. The non-transitory machine readable medium may include ROMs, EPROMs, EEPROMs, flash memories and optical disks. The term processor is intended to include devices such as a field programmable gate array (FPGA).

The term "conveyance device" as used above means any device, device component, combination of devices, media and/or member that may be used to convey, house, support or otherwise facilitate the use of another device, device component, combination of devices, media and/or member. Exemplary non-limiting conveyance devices include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. The term "information" as used above includes any form of information (Analog, digital, EM, printed, etc.). The term "processor" or "information processing device" herein includes, but is not limited to, any device that transmits, receives, manipulates, converts, calculates, modulates, transposes, carries, stores or otherwise utilizes information. An information processing device may include a microprocessor, resident memory, and peripherals for executing programmed instructions. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on. Thus, configuration of the processor may include operative connection with resident memory and peripherals for executing programmed instructions.

As used herein, the term "fluid" and "fluids" refers to one or more gasses, one or more liquids, and mixtures thereof. A "fluid" as used herein includes any gas, liquid, flowable solid and other materials having a fluid property. A "downhole fluid" as used herein includes any gas, liquid, flowable solid and other materials having a fluid property and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, engineered fluids, oils and solvents used in conjunction with downhole tools, water, brine, and combinations thereof. An "engineered fluid" may be used herein to mean a human made fluid formulated for a particular purpose.

Method embodiments may include conducting further operations in the earth formation in dependence upon the formation resistivity information, the logs, estimated parameters, or upon models created using ones of these. Further operations may include at least one of: i) extending the borehole; ii) drilling additional boreholes in the formation; iii) performing additional measurements on the formation; iv) estimating additional parameters of the formation; v) installing equipment in the borehole; vi) evaluating the formation; vii) optimizing present or future development in the formation or in a similar formation; viii) optimizing present or future exploration in the formation or in a similar formation; ix) evaluating the formation; and x) producing one or more hydrocarbons from the formation.

While the foregoing disclosure is directed to the one mode embodiments of the disclosure, various modifications will be apparent to those skilled in the art. It is intended that all variations be embraced by the foregoing disclosure.

What is claimed is:

1. A method of evaluating a fluid, the method comprising:
    transmitting a light beam through the fluid to a detector while oscillating a path length traveled through the fluid by the light beam at a first frequency of oscillation;
    measuring a time-dependent intensity of incident light at the detector responsive to an interaction of the light beam with the fluid to produce a time-dependent intensity signal;
    filtering the time dependent intensity signal to recover a path-dependent signal oscillating at the first frequency and indicative of an absorbance property of the fluid; and
    estimating a parameter of interest of the fluid using the path-dependent signal.

2. The method of claim 1, wherein the time-dependent intensity is indicative of a decrease in intensity between the light beam and the incident light.

3. The method of claim 2, wherein:
    the time-dependent intensity is indicative of a difference in intensity caused by absorbance and a difference in intensity caused by non-absorbance related optical effects; and
    the difference in intensity caused by absorbance is represented by the path-dependent signal.

4. The method of claim 1, comprising filtering the time-dependent intensity signal using at least one of: i) a band-pass filter centered on a second frequency substantially the same as the first frequency; and ii) a phase-sensitive lock-in amplifier.

5. The method of claim 1, wherein the parameter of interest comprises at least one of: i) an oil fraction of the fluid; ii) a water fraction of the fluid; iii) a gas fraction of the fluid; and iv) a composition of the fluid.

6. The method of claim 1, wherein the path length is oscillated between a minimum path length and a maximum path length, the minimum path length corresponds to a maximum in the path-dependent signal, and the maximum path length corresponds to a minimum in the path-dependent signal.

7. The method of claim 6, estimating the parameter of interest by using a ratio of a first intensity of the minimum in the path-dependent signal to a second intensity of the maximum in the path-dependent signal to estimate an absorbance of the fluid.

8. The method of claim 6, wherein the difference between the minimum path length and the maximum path length is a non-zero value less than one millimeter.

9. The method of claim 1, wherein at least one of i) transmitting the light beam through the fluid, and ii) measuring the time-dependent intensity of incident light at the detector, is carried out using an optical fiber immersed in the fluid.

10. The method of claim 1, wherein oscillating the path length comprises moving at least one of a source of the light beam and the detector along a light beam axis with respect to the other of the source and the detector.

11. The method of claim 1, comprising estimating the parameter of interest using spectral information from the incident light.

12. The method of claim 1, wherein the downhole fluid is flowing.

13. The method of claim 1, comprising estimating an absorbance from the path-dependent signal, and using the absorbance to estimate the parameter of interest.

14. The method of claim 1, wherein the fluid is a highly scattering mixture.

15. An apparatus for evaluating a fluid, the apparatus comprising:
    a spectral detector;
    a light source configured to transmit a light beam through the fluid to the detector;
    an actuator configured to oscillate a path length traveled through the fluid by the light beam at a first frequency of oscillation; and
    at least one processor configured to:
        measure a time-dependent intensity of incident light at the detector responsive to an interaction of the light beam with the fluid to produce a time-dependent intensity signal;
        filter the time dependent intensity signal to recover a path-dependent signal oscillating at the first frequency and indicative of an absorbance property of the fluid; and
        estimate a parameter of interest of the fluid using the path-dependent signal.

* * * * *